US012778427B2

(12) United States Patent
Carver et al.

(10) Patent No.: US 12,778,427 B2
(45) Date of Patent: Nov. 3, 2026

(54) MULTISPECTRAL IMAGING OF INTRINSIC METABOLIC FLUOROPHORES FOR THE IN-VIVO DETECTION OF HUMAN BREAST CANCER

(71) Applicant: Philadelphia Lightwave, LLC, New Egypt, NJ (US)

(72) Inventors: Gary E. Carver, Wilmington, VT (US); Mark D. Entwistle, New Egypt, NJ (US)

(73) Assignee: Philadelphia Lightwave, LLC, New Egypt, NJ (US)

( * ) Notice: Subject to any disclaimer, the term of this patent is extended or adjusted under 35 U.S.C. 154(b) by 66 days.

(21) Appl. No.: 18/961,869

(22) Filed: Nov. 27, 2024

(65) Prior Publication Data

US 2026/0144445 A1 May 28, 2026

(51) Int. Cl.
*A61B 5/00* (2006.01)
*G06T 7/00* (2017.01)

(52) U.S. Cl.
CPC .......... *A61B 5/0071* (2013.01); *A61B 5/4312* (2013.01); *G06T 7/0012* (2013.01); *G06T 2207/10024* (2013.01); *G06T 2207/30068* (2013.01); *G06T 2207/30096* (2013.01)

(58) Field of Classification Search
CPC ................ A61B 5/0071; A61B 5/4312; G06T 7/0012; G06T 2207/10024; G06T 2207/30068; G06T 2207/30096
See application file for complete search history.

(56) References Cited

PUBLICATIONS

Waterhouse et al. Enhancing intraoperative tumor delineation with multispectral short-wave infrared fluorescence imaging and machine learning. Journal of Biomedical Optics, vol. 28, Issue 9, 094804. Mar. 2023 (Year: 2023).*

* cited by examiner

*Primary Examiner* — Amelie R Davis
(74) *Attorney, Agent, or Firm* — Connelly Law PLLC; Jonathan B. David

(57) ABSTRACT

A method includes applying a focused laser beam onto a target region. The method can also include obtaining images of a plurality of spectral bands of fluorescence induced by the applied laser beam onto the target region. In addition, the method can include determining from the images, a value for each pixel, wherein the value is based on a dimensional vector that represents a spectral shape of a tumor in the target region. Further, the method includes merging the images of the plurality of spectral bands into a single image based on an assigned color for each pixel and a grey level of the images.

14 Claims, 10 Drawing Sheets

MULTISPECTRAL IMAGING OF INTRINSIC METABOLIC FLUOROPHORES FOR THE IN-VIVO DETECTION OF HUMAN BREAST CANCER

BACKGROUND

Field

Embodiments of the present invention generally relate to using multispectral images of intrinsic fluorescence to detect breast cancer in patients.

Description of Related Art

There are currently over 310,000 breast cancer patients per year in the United States. About 60 percent of these patients have lumpectomies, and 20 to 30 percent of the lumpectomies are followed by additional surgical excision within several weeks. Tumors can be localized before surgery utilizing mammography or ultrasound and subsequent placement of a device such as a wire, radio frequency identification (RFID) clip or radioactive seed. Intraoperative digital specimen mammography can be used to assess margins, although residual cancer at the cellular level near the tumor's location is not easily detected. Conventional practice can also rely on intraoperative assessments of surgical margins by pathologists, though this method is time consuming. As a result, follow-up surgeries are often required due to insufficient surgical margin guidance during the initial lumpectomy. This issue is further exacerbated when DCIS (ductal carcinoma in-situ) is present, and forces patients to face protracted periods of concern, morbidity, and increased costs.

Surgeons could reduce the number of follow-up surgeries if a sensitive and rapid technique was available for intraoperative surveys of the surgical cavity. Many technical efforts have been directed at this problem with varying levels of success. The ideal technique would analyze the entire surgical cavity with high spatial resolution, sensitivity, and specificity in less than a couple of minutes. Leading techniques include optical coherence tomography (OCT), mass spectrometry, radio-frequency (RF) spectroscopy, and extrinsic fluorescence. These techniques rely on differences between tumors and healthy tissue-including optical scatter, dielectric properties, the concentration of metabolites, and the uptake of fluorescent labels. Each technique has caveats. The OCT scans must be read by pathologists. The RF method has been used to reduce follow-up surgeries by 50 percent, though only reveals features over 0.8 millimeters (mm) in size. Scans of extrinsic fluorescence have reduced re-excision rates by 19 percent. However, even with these advancements, there are still over 30,000 patients undergoing follow-up surgeries in the US every year. The time required for each technique depends on the seconds per image or scan, and the number of images or scans required to survey the surgical cavity. A useful optical technique would be expected to survey the entire surgical cavity in less than about 3 minutes.

Accordingly, a technique is needed to more effectively detect breast cancer in women and men without the disadvantages of the current techniques. A technique is needed that can detect cancer levels in the breast region in a more time-efficient and cost-efficient manner.

SUMMARY

Embodiments in accordance with the present invention provide a method for identifying cancer in a target region.

The method includes applying a focused laser beam onto the target region. The method can also include obtaining images using a plurality of spectral bands of fluorescence induced by the applied laser beam onto the target region. Further, the method can include determining from the images, a value for each pixel, wherein the value is based on a dimensional vector that represents a spectral shape of fluorescence from a tumor in the target region. In addition, the method can include merging the images of the plurality of spectral bands into a single image based on an assigned color for each pixel and a grey level derived from the plurality of black and white images.

The plurality of spectral bands include fluorescence from nicotinamide adenine dinucleotide (NADH) and flavin adenine dinucleotide (FAD).

Embodiments in accordance with the present invention provide a method of identifying cancer in a target region. The method can include configuring the target region to receive a focused laser beam. The method can also include applying the laser beam onto the target region. Further, the method can include obtaining, based on the applied laser beam onto the target region, a plurality of images representing a plurality of spectral bands. The method can further include identifying a value of each pixel of the plurality of spectral bands, wherein the value is determined based on a difference between a known vector that represents a spectral shape of the plurality of spectral bands on a tumor in the target region and a normalized signal strength. The method can also include identifying whether the cancer is prevalent for each pixel based on the identified value that indicates an assigned color for each pixel.

The method can also include comparing the value derived from each pixel to an adjustable numerical constant to determine the prevalence of the cancer for each pixel.

Embodiments in accordance with the present invention include a system to identify cancer levels in a target region. The system can include a laser device that applies a focused laser beam onto the target region. The system also includes a controller that obtains images of a plurality of spectral bands induced by the laser beam applied onto the target region. Further, the system includes a processor that determines from the plurality of black and white images, a value for each pixel in the image. The value is based on a dimensional vector that is used to compute the difference between the spectral shape of a tumor in the target region and a signal strength. The processor can also identify a prevalence of the cancer for each pixel based on the determined value for each pixel. The system further includes electronics and firmware that merge the images of the plurality of spectral bands into a single image based on an assigned color for each pixel and a grey level of the images.

The laser device can be configured to a single micron spot on the target region for a set time interval.

These and other advantages will be apparent from the present application of the embodiments described herein.

The preceding is a simplified summary to provide an understanding of some embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The above and still further features and advantages of embodiments of the present invention will become apparent upon consideration of the following detailed description of embodiments thereof, especially when taken in conjunction with the accompanying drawings, and wherein.

Figure 1:
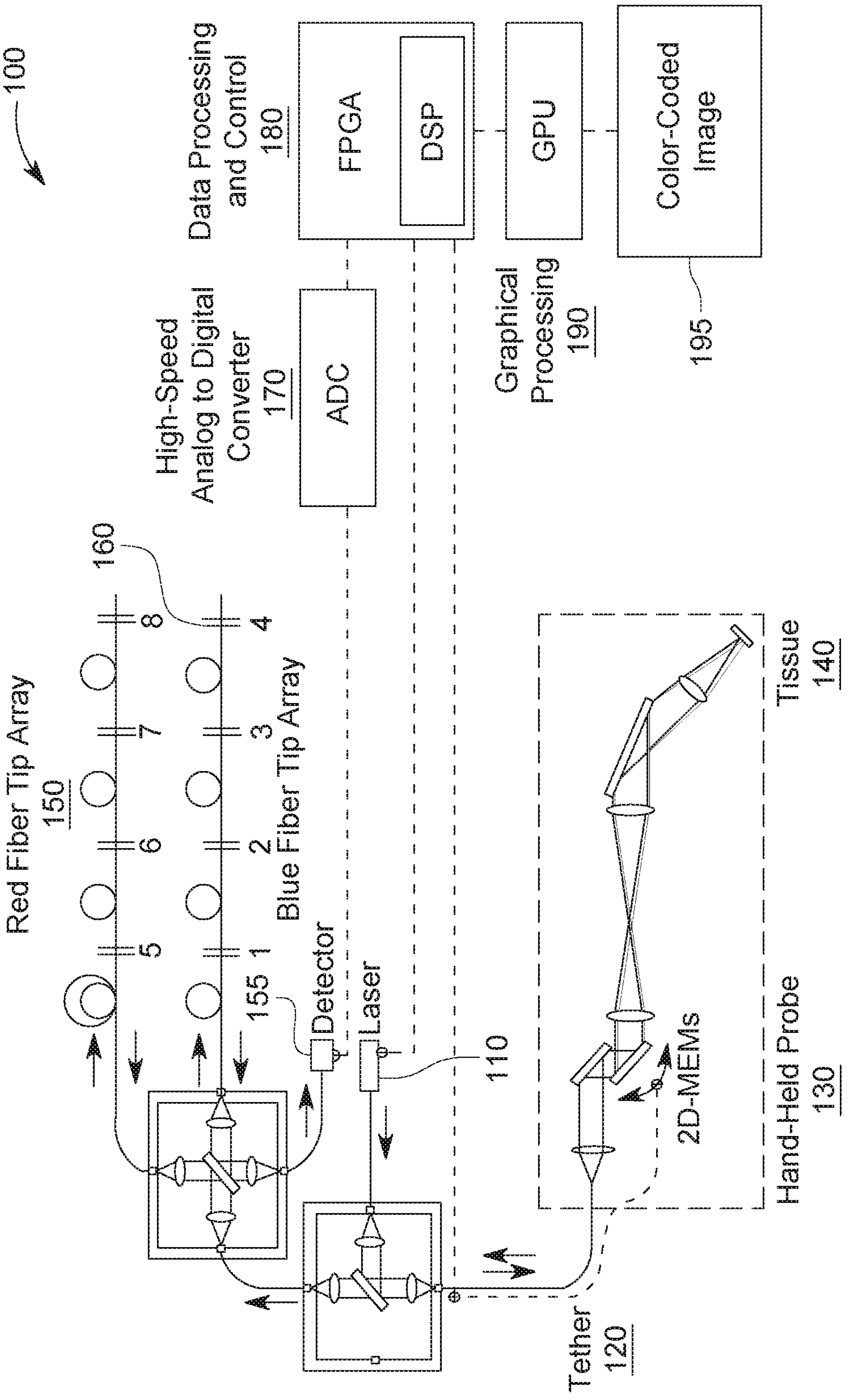
FIG. 1 illustrates a side view of a system according to an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

Multispectral imaging of intrinsic fluorescence can be applied to detect breast cancer in the breast regions of patients. Intrinsic fluorescence can be sensitive to the biochemistry of cancer cells before and after they form tumors. The lactic acid cycle in cancer cells can influence the cytosolic concentration of metabolic fluorophores including nicotinamide adenine dinucleotide (NADH) and flavin adenine dinucleotide (FAD). The incidence or prevalence of cancer can result in the magnitude of fluorescence in NADH to increase up to 1.5× or more, while the magnitude of fluorescence of FAD can be reduced. A multi-spectral imaging system has been developed to analyze intrinsic fluorescence from the NADH and FAD bands.

Spectra for each pixel in images can be collected in 2.5 microseconds. Practical fields of view can be scanned in one second. As such, a medical professional can use a hand-held device to emit a laser beam into a target region of a patient. The target region can be the breast region of a female or male patient. The hand-held design can scan a 5 mm field at a rate of 1 second per frame. This optical design leverages a two-dimensional micromechanical scanning mirror and miniaturized optics to emulate the shape of other hand-held designs. The fluorescence of the emitted laser can be received by a detector in the system. An analog electrical signal from the detector can be digitized by an analog-to-digital (ADC) converter. Data can therefore arrive serially in a front end of a field-programmable gate array (FPGA). Deserialization and registration of the images can occur. In addition, images at each of a plurality of spectral bands can be obtained.

A digital signal processor (DSP) and FPGA within a Data Processor and Control board can determine a spectrum using the plurality of spectral bands for each pixel location. The DSP can determine a value for each pixel that is equal to the difference between a known spectrum and an observed spectrum for the location of each pixel. The DSP can assign a color based on the determined value of each pixel. Moreover, the color-coding method is based on establishing an eight-dimensional vector ($V_N$ where N=1–8) that represents the spectral shape of the eight spectral bins acquired on a known tumor. During real time operation, the value of Δ can be computed for each pixel, where $\Delta=\Sigma|S_N-V_N|$, and $S_N$ is the normalized signal strength for each bin. The color of each pixel in the color-coded image is based on the following: red if Δ<Num, yellow if Δ<2 Num, green if Δ<3 Num, cyan if Δ<4 Num, and blue if Δ<5 Num. The value of Num (0.55 in this work) is set such that red colored pixels indicate cancer. For example, if each bin contributes the same amount to the value of Δ, then each bin in $S_N$ differs from the bins in $V_N$ by 0.55/8=0.07 or 7%. A key issue is the stability of $V_N$ and Num across patient populations.

The assigned color for each pixel can indicate the prevalence of cancer, pre-cancerous regions, and/or healthy regions. A grey-scale image is generated for each of the eight spectral bands. A single image can then be created from the plurality of images. Custom electronics and firmware merge the eight images into one color-coded image for use by the surgeon in real time. The DSP can perform a handoff to a graphical processing unit (GPU) to enable a single color-coded image to be produced from merging the plurality of images. The single color-coded image can then be produced and given to the medical professional for viewing. The medical professional can view the single color-coded image and identify the healthy regions and also any regions where cancer is prevalent. The process described above can be used to detect various forms of cancer.

Referring to FIG. (FIG.) 1, a multi-spectral imaging system (system) 100 is illustrated to treat a breast region of patients. In other embodiments using fiber optic endoscopes, other regions of the patients can be treated with respect to other cancers and ailments. The field of view can be adjusted either up or down with respect to the target region. The patients can include female or male patients in various embodiments. The system 100 can include a laser device 110 that can emit or transmit a laser beam across the patient while florescence induced by the laser beam is directed to a fiber tip that can serve as a confocal pinhole. The hand-held probe 130 can be held by medical professionals in one or more places. In various embodiments, the hand-held probe 130 can be covered with a transparent sheath to act as a viral or bacterial barrier. The laser device 110 can emit a single laser at a wavelength of three hundred and seventy-five nanometers (nm). The medical professional can hold the hand-held probe 130 near the treatment region as tissue receives the laser and emits fluorescence. The laser can travel through a tether 120 and into a hand-held probe 130. The laser beam can reach a tissue 140 within a patient. In many embodiments, the tissue 140 can be the breast region or area of the patient. Other portions of the body and other cancers can be treated in various embodiments. The patient can be both men and women in various embodiments.

Referring to FIG. 1, the laser device 110 can emit a laser beam that is transmitted through the tether 120, hand-held probe 130 and onto the tissue 140. The fluorescence induced by the laser can be transmitted through a laser spitter and onto the red and blue fiber tip arrays 150, 160. The portions of the fluorescence in the red array range can go to a tip in the red fiber tip array 150. The portions of the fluorescence in the blue array range can go to a tip in the blue fiber tip array 160. Each tip in the red and blue fiber tip arrays 150, 160 reflect a portion of the red and blue range of fluorescence, and enable the fluorescence to move onto the detector 155. Eight spectral bands can result from the red and blue ranges of the fluorescence that flow into the detector 155. In this discussion red and blue refer to the longer and shorter wavelengths of the fluorescence respectively. The fluorescence can be detected by the detector 155. The analog electrical signal from the detector 155 can flow into a high-speed analog to digital convertor (ADC) 170. The ADC 170 can receive analog electrical signals from the detector 155. The ADC 170 can digitize the analog electrical signal(s). Data can then arrive serially at the FPGA within the Data Processing and Control Board 180 at the front end of the FPGA. There can be a deserialization and registration of the plurality of images. Images at a plurality of the spectral bands can thereby be obtained. The spectral bands can be the eight bands marked in FIG. 2B.

In FIG. 1, the DSP can also be configured within the Data Processing and Control Board 180. The DSP can determine a spectrum using the plurality of spectral bands for each pixel location. The DSP can determine a value for each pixel. The DSP can determine the value that is equal to difference between a known spectrum and the observed spectrum for the location of each pixel. The DSP can perform various calculations for each pixel in the plurality of images to determine whether cancer is represented by any of the pixels. A color can be determined for each pixel of the single color-coded image. Moreover, the color-coding can be based on establishing an eight-dimensional vector $V_N$, where N=1–8. Further, $V_N$ can represent the spectral shape of eight spectral bins acquired on a known tumor that can be positioned in or around the tissue 140. During the real-time operation of the system 100, the value of Δ can be computed for each pixel, where $\Delta=\Sigma|S_N-V_N|$, and $S_N$ is the normalized signal strength for each bin. The color of each pixel in the color-coded image is based on the following: red if $\Delta<$Num, yellow if $\Delta<2$ Num, green if $\Delta<3$ Num, cyan if $\Delta<4$ Num, and blue if $\Delta<5$ Num. As such, the color of each pixel in the single color-coded image can be based on the following: red if $\Delta<$Num, yellow if $\Delta<2$ Num, green if $\Delta<3$ Num, cyan if $\Delta<4$ Num, and blue if $\Delta<5$ Num. The value of the constant Num is 0.55. For various patient populations, the value of Num can be greater or less. A value for Δ can be calculated for each pixel.

In FIG. 1, each pixel in the color-coded image that has a value for Δ that falls on red will be held to represent cancer. In addition, each pixel with a value of Δ of yellow can be held to be pre-cancerous. Other values Δ that fall under blue, green, or cyan can be held to be non-cancerous. The DSP can assign a color to each pixel based on identified value for each pixel. The plurality of images can be merged into a single image after a color has been assigned to each pixel. The DSP can perform a handoff with the GPU 190 to enable the single image to be formed from the plurality of images. Once the single image is formed, the single image can be presented to the medical professional for viewing. The medical professional can view which part of the image represents cancer regions, and which part of the image represents pre-cancer regions or healthy regions.

Figure 2A:
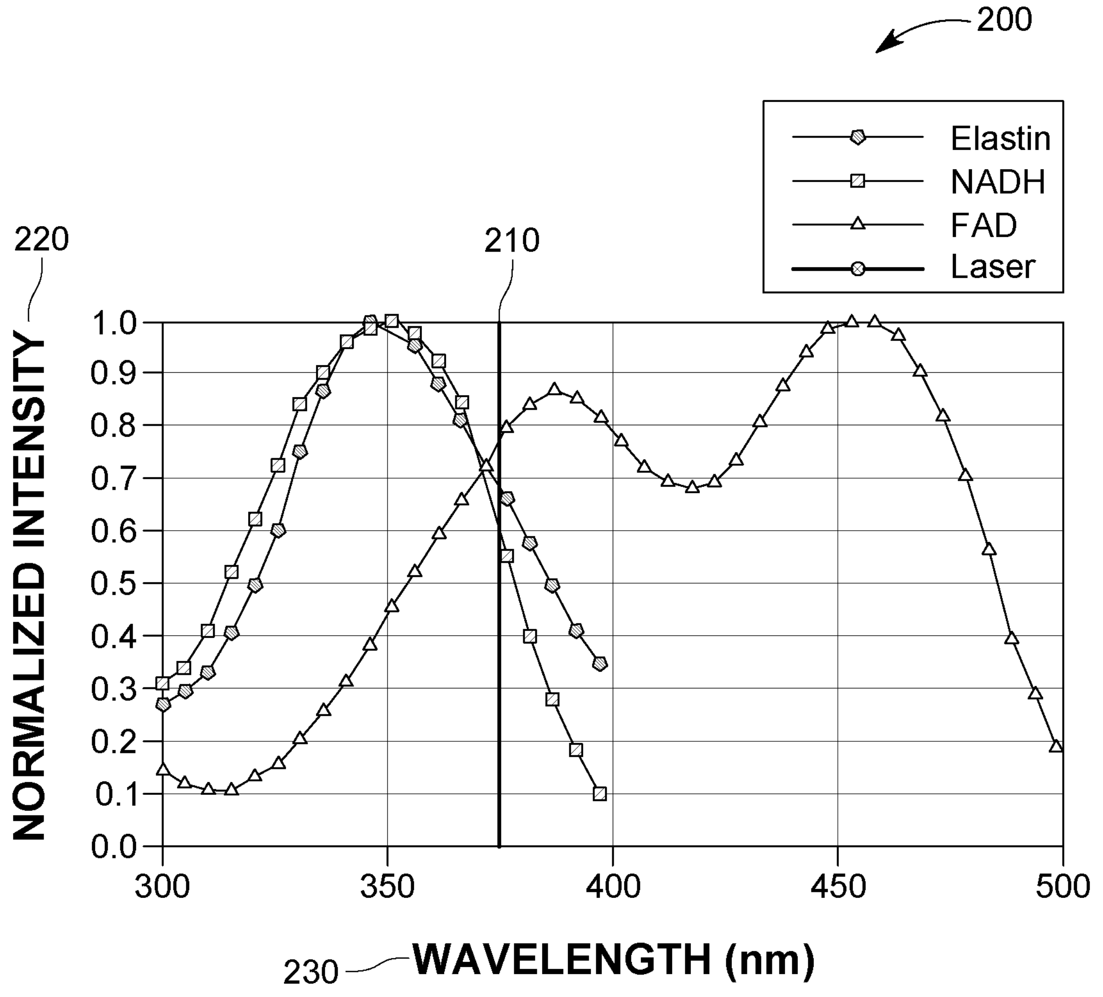
FIG. 2A illustrates a graph according to an embodiment of the invention.
Figure 2B:
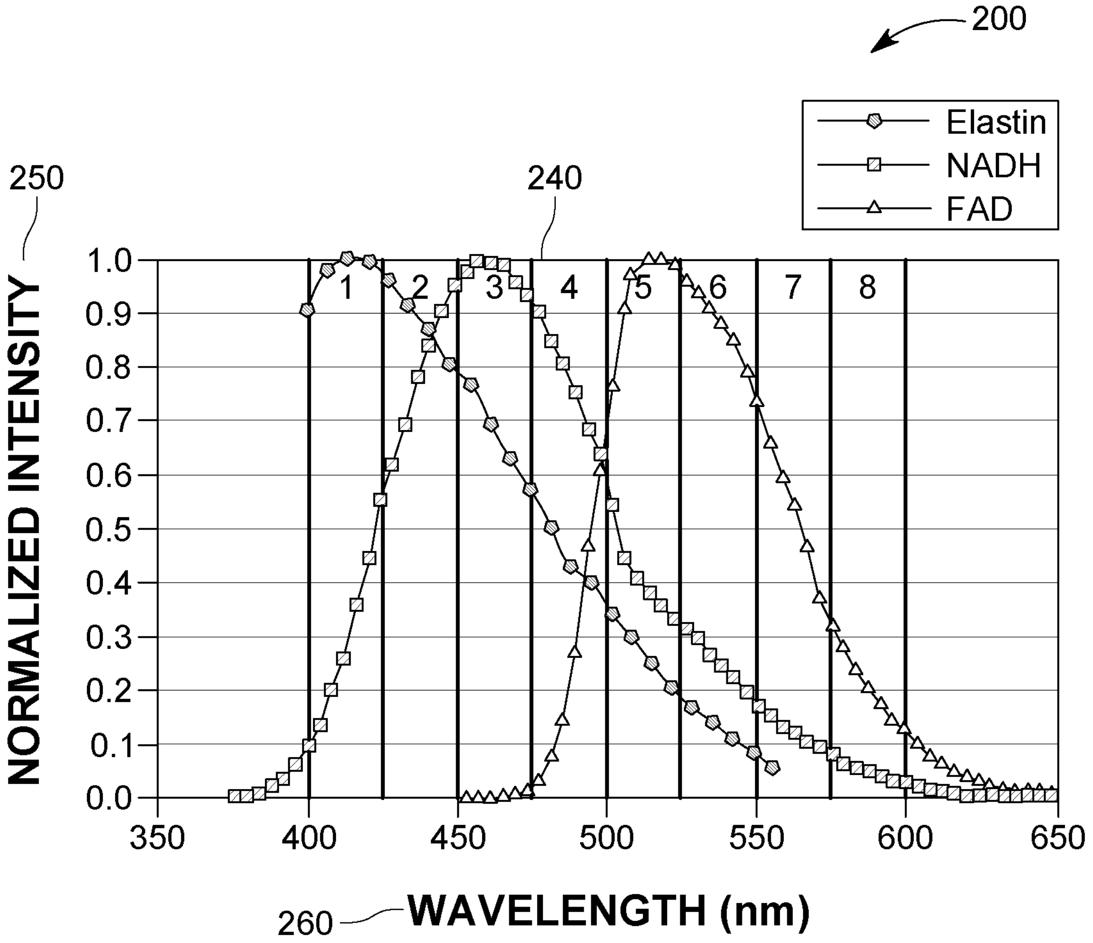
FIG. 2B illustrates a graph according to an embodiment of the invention.

In FIGS. 2A-2B, a system 200 with graphs 210 and 240 are illustrated based on the application of the system 100 described in FIG. 1. The graphs 210, 240 have a normalized intensity 220, 250 and wavelength 230, 260.

With respect to FIG. 2A, the graph 210 illustrates the normalized proportion of laser intensity that is absorbed by NADH, FAD, and elastin. Further, it is illustrated how the wavelength of the laser is set at three hundred and seventy-five nm. Breast cancer as evidenced by red pixels can increase the magnitude of fluorescence from NADH by a factor of 1.5 or more, while reducing the fluorescence of FAD.

Referring to FIG. 2B, the graph 240 illustrates the normalized intensity 250 and wavelength 260 of the laser induced fluorescence of elastin, NADH, and FAD over eight spectral bands. As in the graph 210, the wavelength of the FAD is greater than NADH. With the onset of breast cancer, the magnitude of fluorescence of the NADH can increase by 1.5 times or more while the fluorescence of FAD can decrease accordingly.

In FIGS. 3A-3D, a system 300 of images and graphs are illustrated based on the application of the system 100 in FIG. 1. The images can illustrate data taken from treatment regions (breast regions) of patients that have several clusters of invasive lobular cancer cells.

Figure 3A:
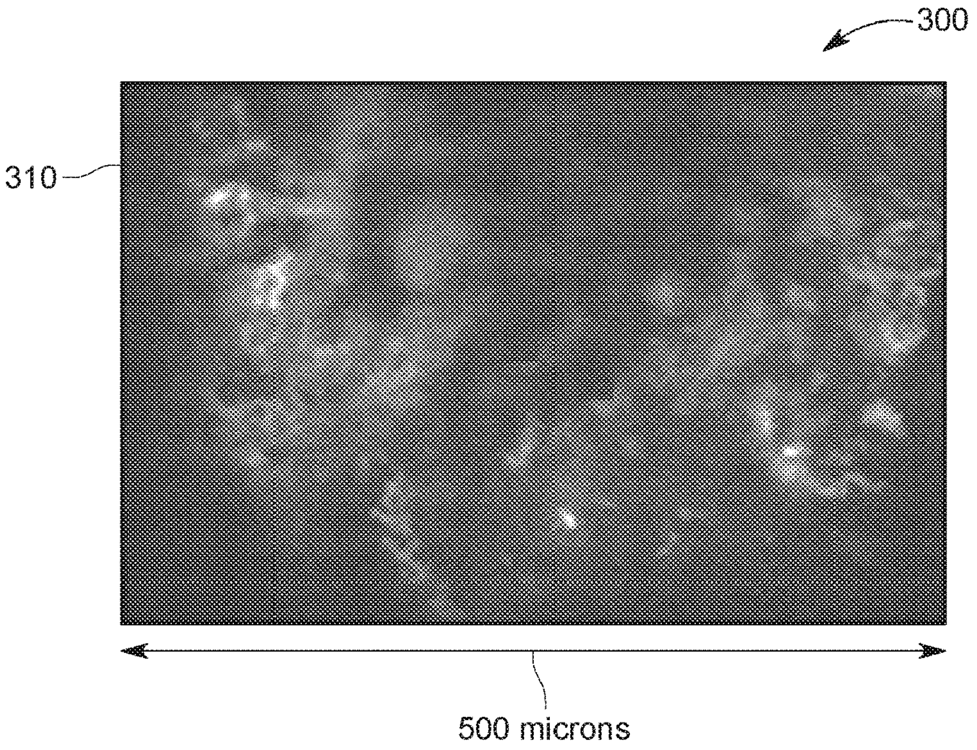
FIG. 3A illustrates an image according to an embodiment of the invention.

Accordingly, in FIG. 3A, image 310 illustrates the brightest of eight spectral bins. The brightest of the eight spectral bins can indicate the fluorescence induced by the laser directed onto the tissue region.

Figure 3B:
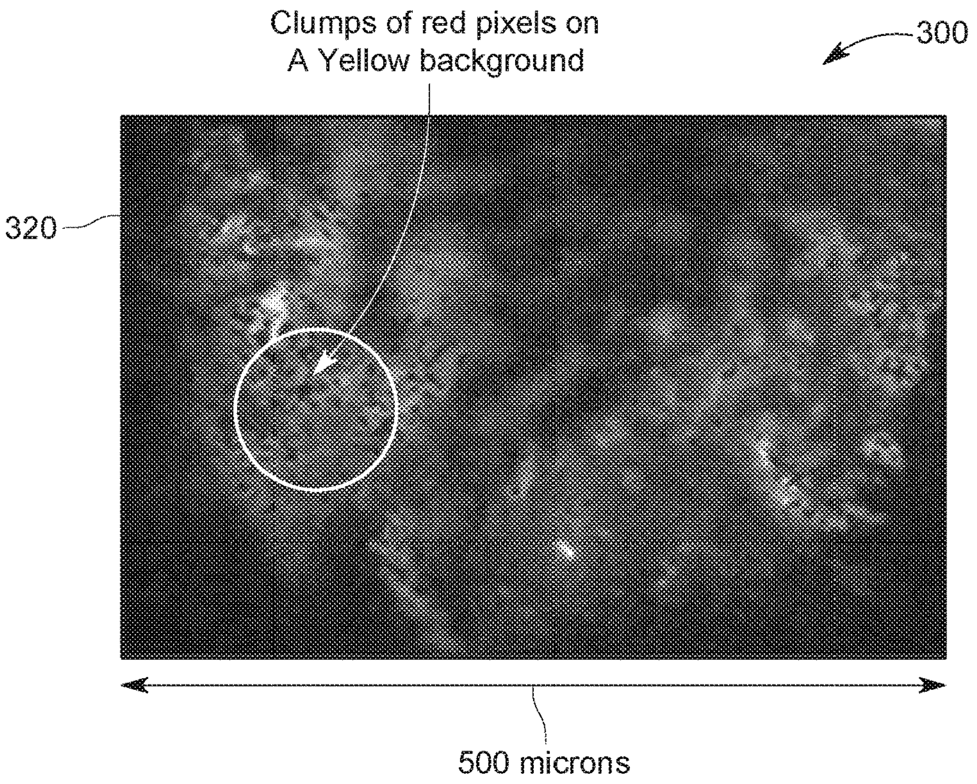
FIG. 3B illustrates another image according to an embodiment of the invention.

In FIG. 3B, the image 320 is the color-coded image that illustrates several red blotches that indicate cancer. As mentioned above, the red pixels identified from the spectra from the plurality of images can indicate cancer.

Figure 3C:
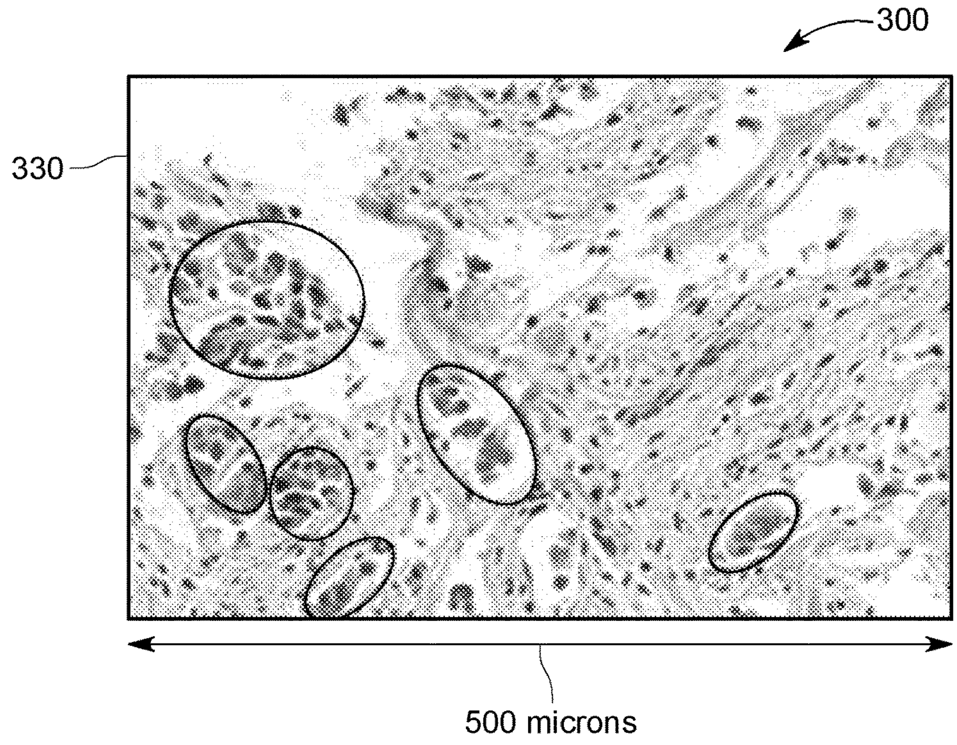
FIG. 3C illustrates an image according to an embodiment of the invention.

Referring to FIG. 3C, image 330 illustrates standard pathological optical microscopy of a stained specimen over a five hundred micron field. The red circles in image 330 and ovals in graph 330 mark the location of tumor cells in the patient. The tumor cells are be surrounded by collagen and lymphocytes.

Figure 3D:
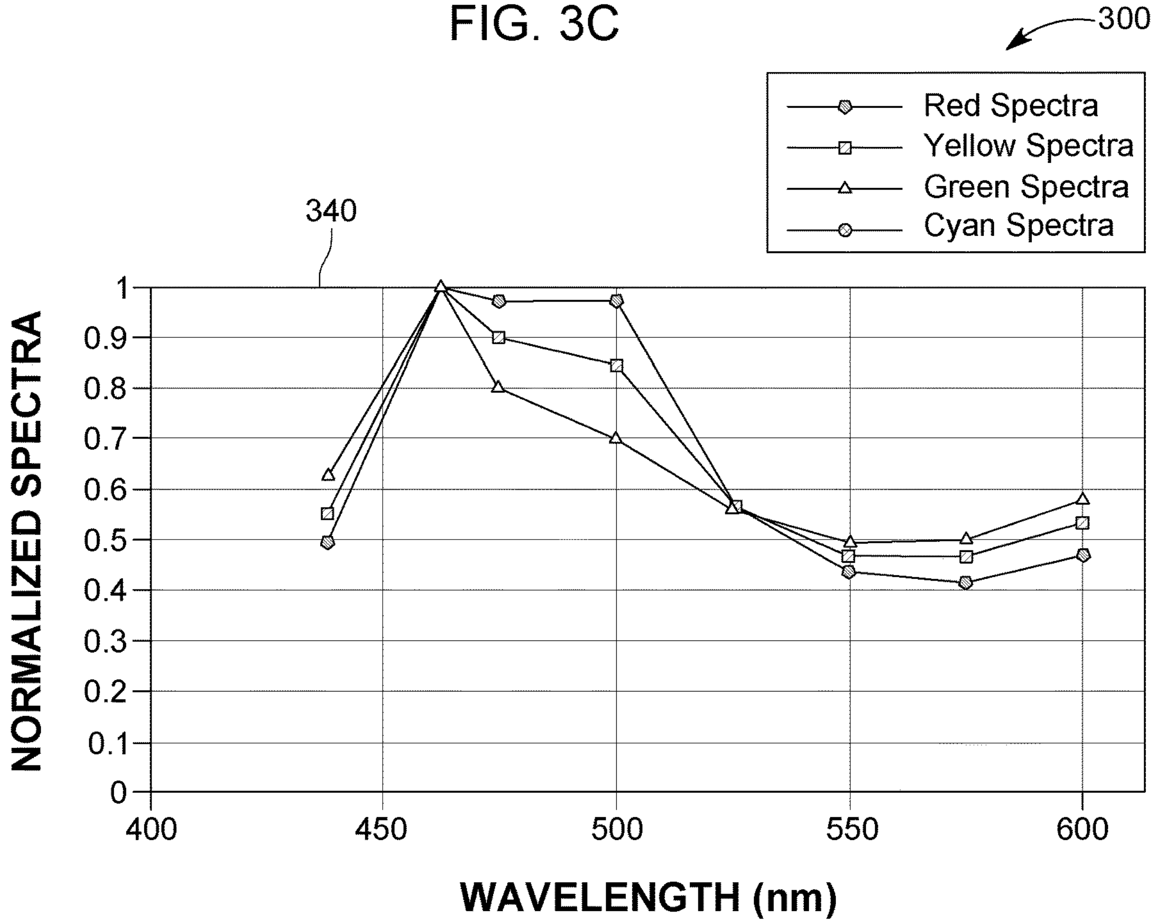
FIG. 3D illustrates a graph according to an embodiment of the invention.

In FIG. 3D, the graph 340 indicates normalized values for eight spectral bins corresponding to FIG. 3B. The red/yellow/green labeled curves can correspond to the average of the red/yellow/green pixels indicated in image 320. The red curve can be higher than the yellow and green curves in the NADH band, while the red curve can be lower than the yellow and green curves in the FAD band. Cancer can cause higher fluorescence in the NADH band, and lower fluorescence in the FAD band. Overall, the cancerous and non-cancerous tissue in images and graphs 310-340 can be clear examples of margin detection which systems that use resolutions in the order of one hundred microns can miss. The various images and graphs 310-340 can illustrate the cancerous tissue in the patients with a sensitivity of 90% and the increase of fluorescence in the NADH band and decrease of fluorescence in the FAD band due to the prevalence of cancer in the treatment region of the patient.

Figure 4A:
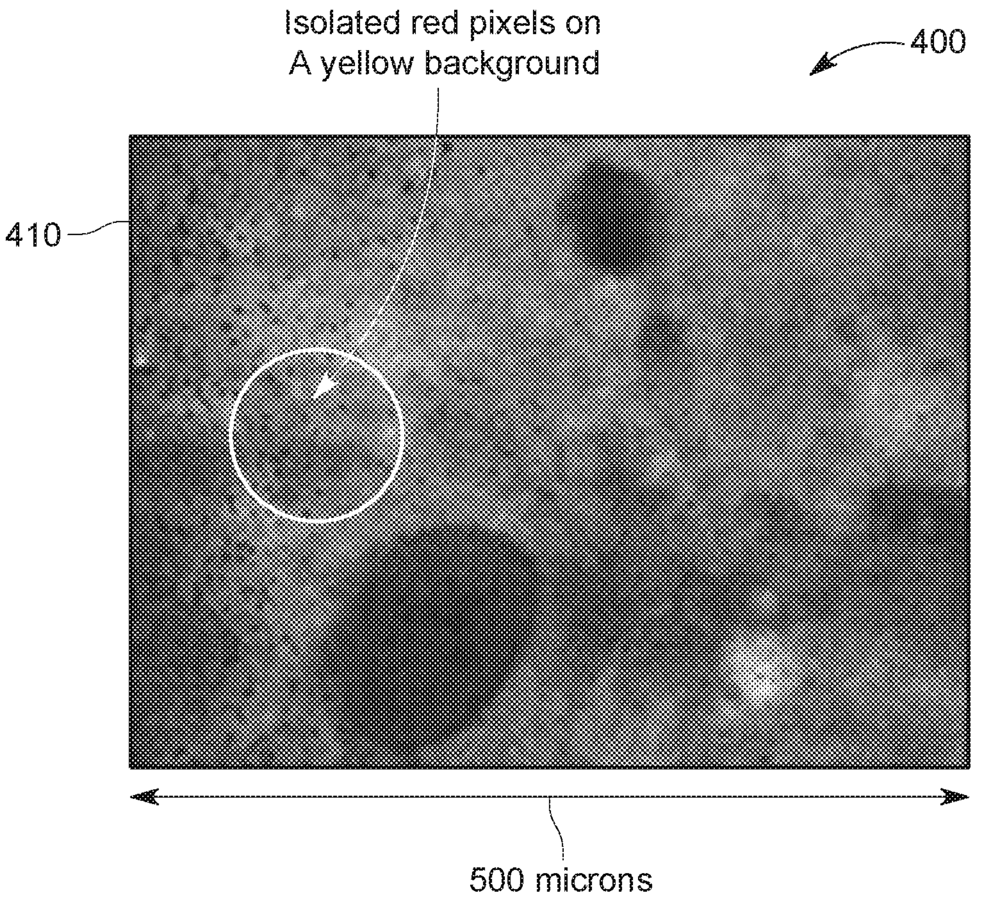
FIG. 4A illustrates an image according to an embodiment of the invention.
Figure 4B:
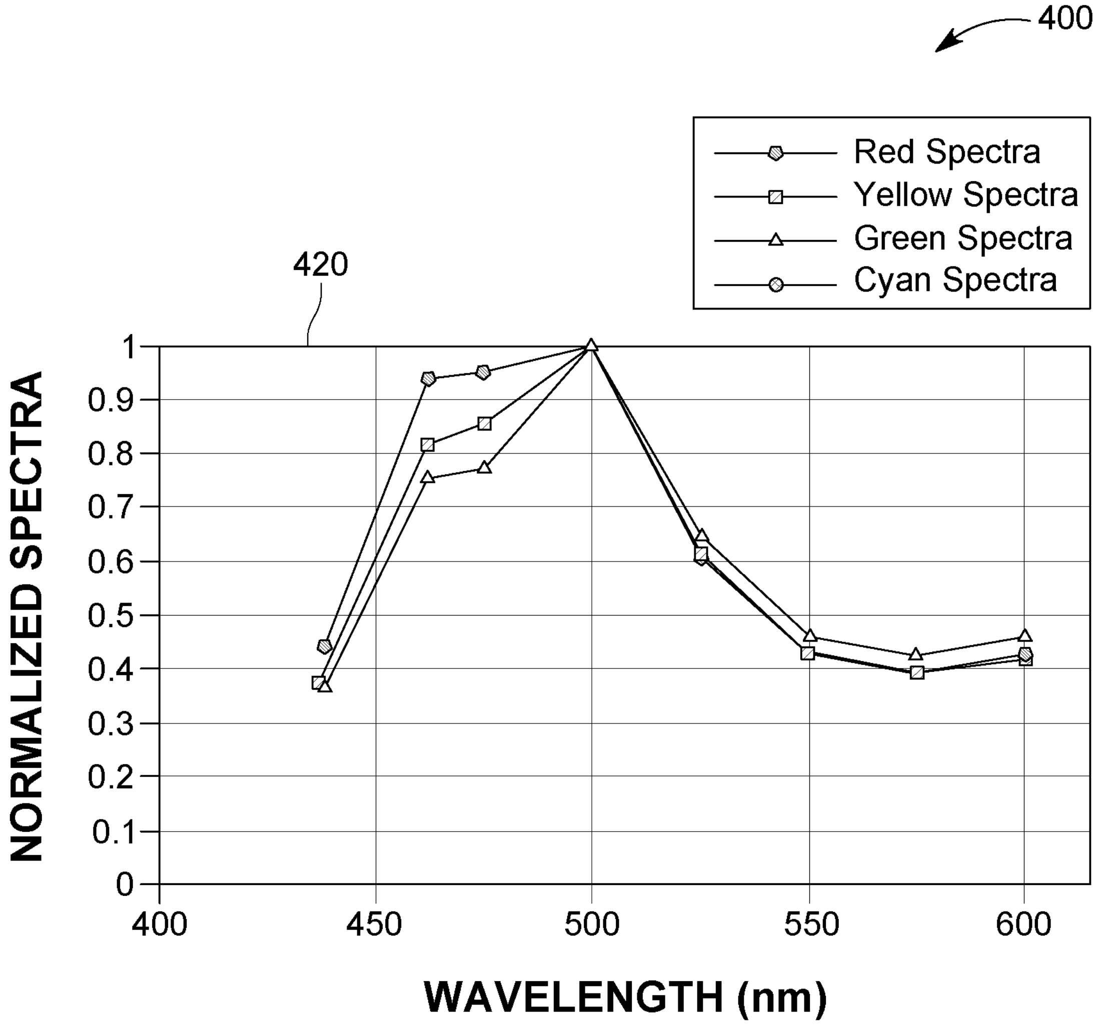
FIG. 4B illustrates a graph according to an embodiment of the invention.

In FIGS. 4A-4B, a system 400 of images and graphs is illustrated where no cancer exists. The system 100 in FIG. 1 can be applied and show no cancer or traces of cancer as well. A high number of pixels from the image of the patient may illustrate no cancer in various embodiments. Pixels which are not identified as red pixels can indicate that no cancer is found.

Referring to FIG. 4A, the image 410 illustrates mostly healthy cells as evidenced by mostly green and yellow pixels over a five hundred micron field. Green pixels can indicate a healthy region. Yellow pixels can also indicate a healthy region. However, in other embodiments, yellow pixels can also indicate pre-cancerous regions as well. The tiny dots in red in the far left of graph 410 can indicate cancer. However, the rest of image 410 indicates mostly non-cancerous regions, although yellow regions could indicate pre-cancerous regions in various embodiments. The image 410 illustrates a small amount of red dots which indicate a small incidence of cancer, or simply noise that can be removed from the image, and mostly non-cancer regions with the green and yellow regions.

In FIG. 4B, the graph 420 plots normalized values for the eight spectral bins corresponding to FIG. 4A. The red spectra, yellow spectra, green spectra, and cyan spectra are illustrated. In the NADH band, the red curve is higher than the yellow, and green curves. In the FAD band, the red curve is below the other curves. The fluorescence of the NADH increases with cancer while the fluorescence of FAD is lower with the incidence of cancer. Overall, pathology indicates dense collagen and a few lymphocytes and the multispectral data indicates no cancer with a specificity of 98.1%.

Figure 5A:
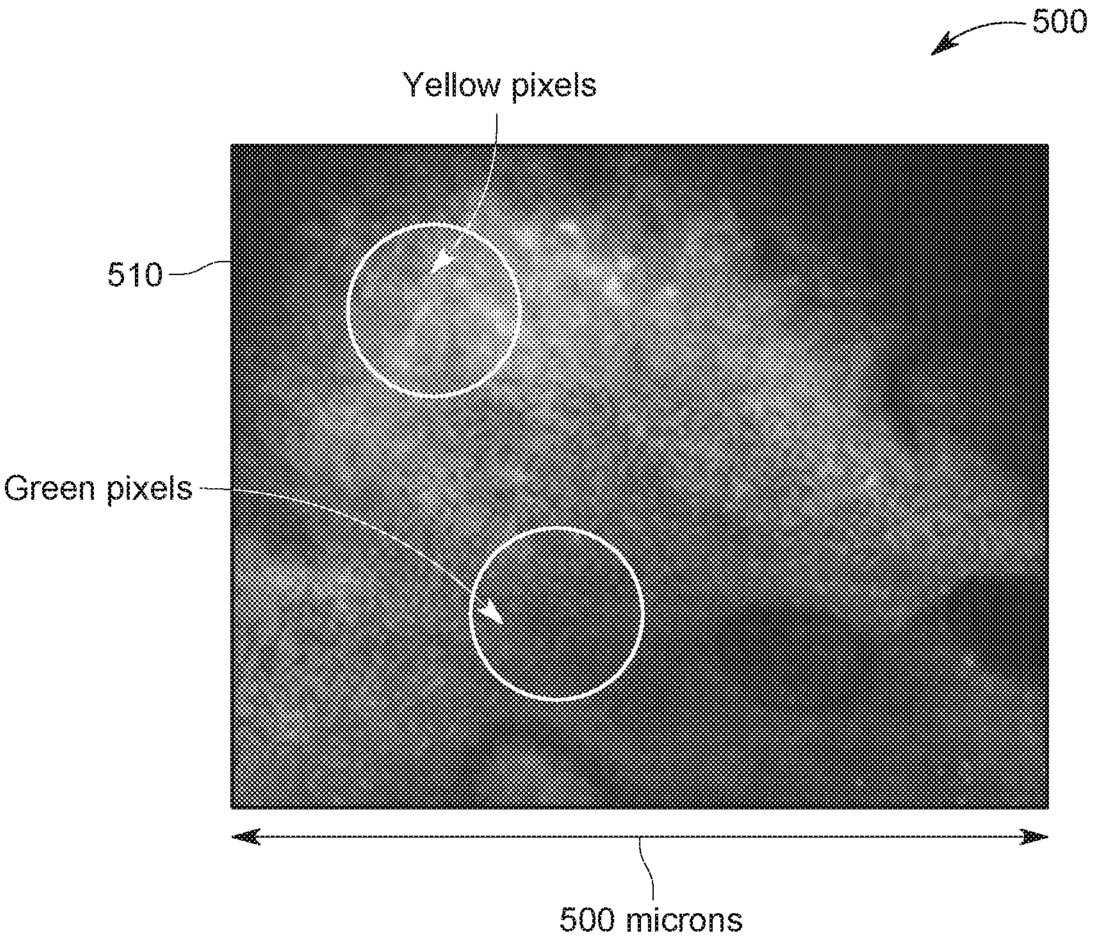
FIG. 5A illustrates yet another image according to an embodiment of the invention.
Figure 5B:
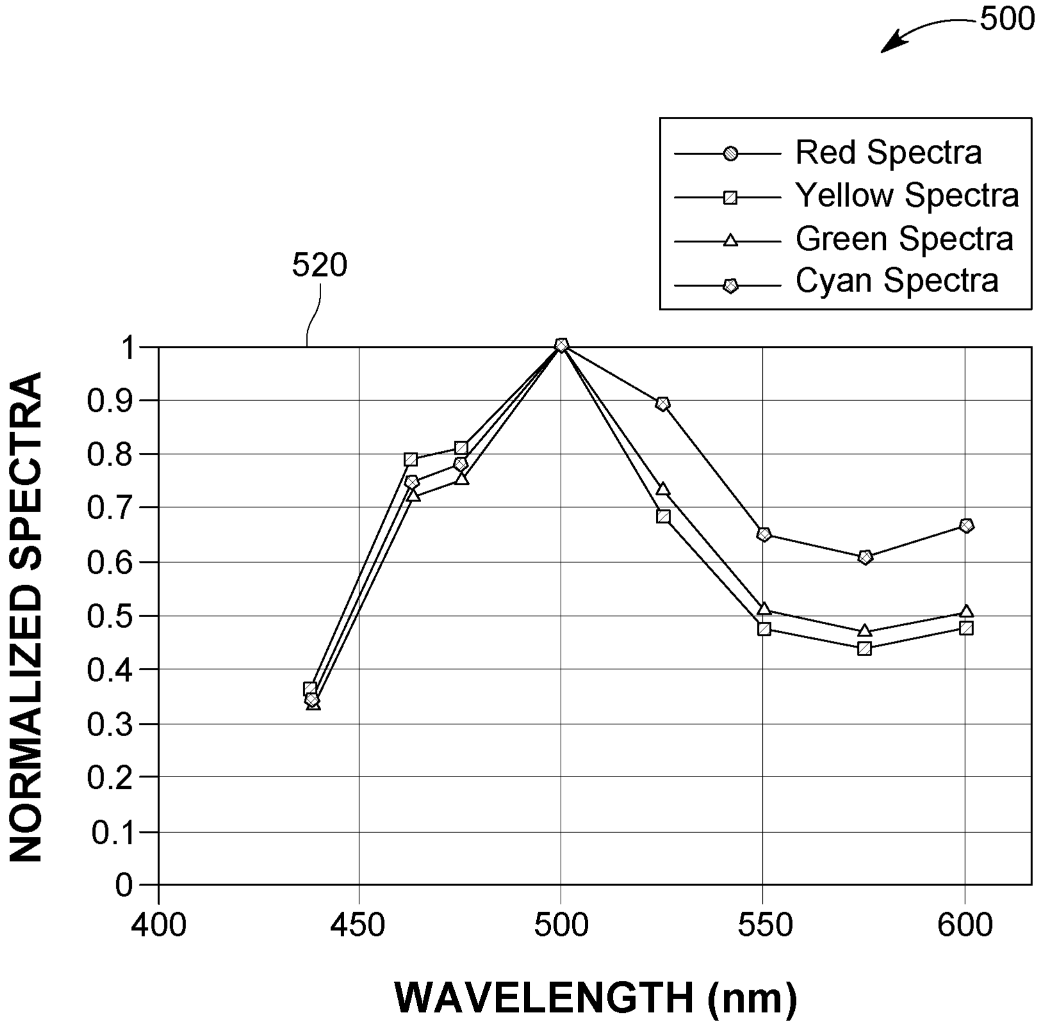
FIG. 5B illustrates another graph according to an embodiment of the invention.

Referring to FIGS. 5A-5B, images and graphs are illustrated with no evidence of cancer. As previously mentioned, the system 100 applied in FIG. 1, can be applied on different patients, and reveal no cancer. The pixels from the spectral of images which do not indicate red would be considered to be non-cancerous regions.

As such, referring to image 510 in FIG. 5A, all of the region indicates non cancer regions. All of the pixels in the plurality of spectral images are colors other than red, and therefore indicate non-cancer regions.

In FIG. 5B, in graph 520, there is an illustration of normalized values for eight spectral bins corresponding to FIG. 5A. There can be insufficient data for a red spectrum. The graph 520 shows a spectrum of yellow, green, and cyan pixels. No red pixels are shown, which thereby indicates no cancer is indicated. Laser scanning of various patients can indicate non-cancer regions. There can be insufficient data for a red spectrum when no pixels in the spectral regions are red. Moreover, while pathology only observes wiry collagen, a few adipocytes and two blood vessels, the multispectral scans detect no cancer with a specificity of 99.9%. Overall, the fluorescence of NADH may not be magnified in the absence of cancer. Further, there can be insufficient data for a red spectrum in the graph 520 when no red pixels are identified in the spectral images.

Figure 6:
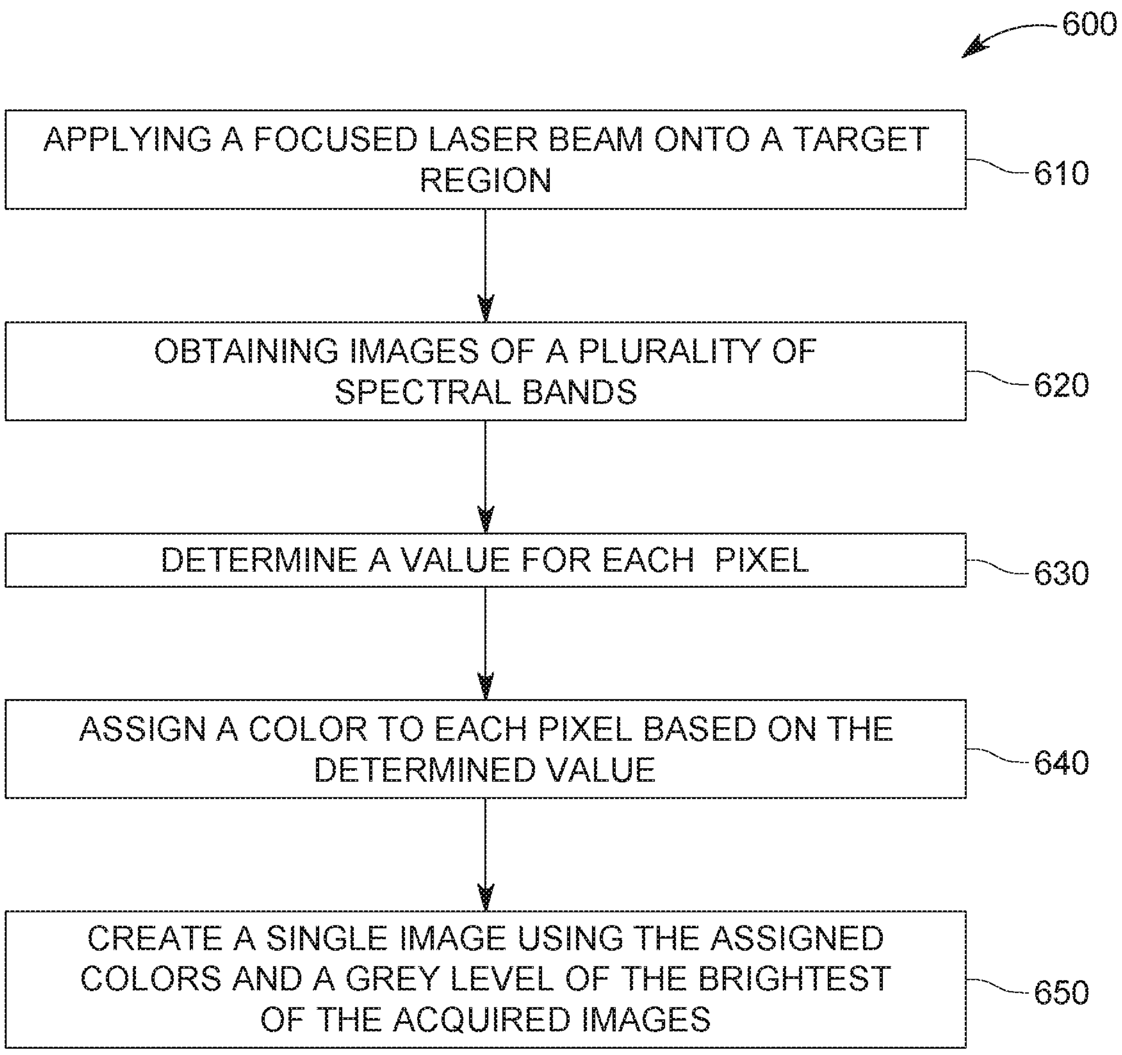
FIG. 6 illustrates a flowchart according to an embodiment of the invention.

In FIG. 6, a process 600 is illustrated for identifying cancer in patients. The cancer can be breast cancer. The treatment region can be the breast region of patients. The patients can be both female and male patients. The patient can be positioned to receive the laser scan to identify the cancer in the patient.

Referring to FIG. 6, at 610, a focused laser beam can be applied into the target region of the patient. A hand-held device can be held by the medical professional. The hand-held device can be positioned near the breast region of the patient. Other portions of the body and other cancers can be treated in various other embodiments. The hand-held device can then emit the laser beam into the breast region of the patient. The fluorescence from the laser can be transmitted back to a series of red and blue fiber tip arrays. The detector can then detect the fluorescence received by the red and blue fiber tip arrays. The electrical signal from the detector can flow into the ADC. The ADC can then digitize the analog electric signal(s) received from the detector. The data can arrive serially into the FPGA. Within the FPGA, deserialization and registration of a plurality of images can occur.

In FIG. 6, at 620, images at each of the plurality of spectral bands can be obtained. There can be a total of eight or more spectral bands. Once the plurality of images are obtained, a determination can be made as to which pixels in the image represent cancer. A spectrum can be determined using the plurality of images for each pixel location by the DSP.

Referring to FIG. 6, at 630, the DSP can determine a value for each pixel. The value can be difference between a known spectrum and the observed spectrum for the location of each pixel. As mentioned previously above, a color can be determined for each pixel of the single color-coded image. Moreover, the color-coding can be based on establishing an eight-dimensional vector $V_N$, where N=1-8. Further, $V_N$ can represent the spectral shape of eight spectral bins acquired on a known tumor that can be positioned in or around the tissue. During the real-time operation of the system, the value of $\Delta$ can be computed for each pixel, where $\Delta=\Sigma|S_N-V_N|$, and $S_N$ is the normalized signal strength for each bin. The color of each pixel in the color-coded image is based on the following: red if $\Delta$<Num, yellow if $\Delta$<2 Num, green if $\Delta$<3 Num, cyan if $\Delta$<4 Num, and blue if $\Delta$<5 Num. As such, the color of each pixel in the single color-coded image can be based on the following: red if $\Delta$<Num, yellow if $\Delta$<2 Num, green if $\Delta$<3 Num, cyan if $\Delta$<4 Num, and blue if $\Delta$<5 Num. The value of the constant Num is 0.55. For various patient populations, the value of Num can be greater or less depending, for example, on patient age and breast density. A value for $\Delta$ can be calculated for each pixel.

In FIG. 6, at 640, the color of each pixel of the plurality of images can be assigned. Moreover, based on the determination of the value for each pixel, the color for each pixel can be assigned. The red pixels can indicate cancer. The yellow pixels can indicate pre-cancer. The green, cyan, and blue pixels and other pixels can indicate no cancer.

In FIG. 6, at 650, a single image is created from the plurality of spectral images. The DSP can perform a handoff to the GPU to enable the single image to be produced from the plurality of images. The single image can be created using the color assigned to the determined value for each pixel and the grey level of the brightest of the acquired images. Noise can also be removed within the DSP and GPU. The produced single image can be produced to the medical professional for viewing. The medical professional can view what part of the single image represents cancerous regions, and what part of the image are non-cancerous regions.

Overall, multispectral imaging of laser induced intrinsic fluorescence is capable of detecting breast cancer in patients without the costs and excessive time of other detection methods. A correlation of color-coded images with pathology demonstrate that images of metabolic fluorophores can provide surgical margin guidance with high sensitivity and specificity. Improved patient outcomes can occur as a clear and concise single image that has merged a plurality of images involving the plurality of spectral bands can provide the medical professional of a clear picture of the cancerous regions, pre-cancerous regions, and healthy regions in the breast region of the patient. There can be improved patient outcomes and reduced costs and time involved in the diagnosis as well. The multispectral imaging of intrinsic fluorescence can provide an efficient means and function to identify breast cancer in patients, and pre-cancer conditions in patients without the excessive costs of current detection systems. With breast cancer surgery escalating to over one billion dollars per year in the USA, multispectral imaging of intrinsic fluorescence can significantly reduce the time and costs involved in detecting and treating breast cancer and other cancers in patients worldwide.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

While the foregoing is directed to embodiments of the present disclosure, other and further embodiments of the present disclosure may be devised without departing from the basic scope thereof. It is understood that various embodiments described herein may be utilized in combination with any other embodiment described, without departing from the scope contained herein. Further, the foregoing description is not intended to be exhaustive or to limit the disclosure to the precise form disclosed.

Modifications and variations are possible in light of the above teachings or may be acquired from practice of the disclosure. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

What is claimed is:

1. A method for identifying cancer in a target region, the method comprising:

applying a focused laser beam onto the target region;

obtaining images using a plurality of spectral bands of fluorescence induced by the applied laser beam onto the target region;

determining from the images, a value for each pixel of each of the images, wherein the value is based on a dimensional vector that represents a spectral shape of a tumor in the target region, and a signal strength; and merging the images of the plurality of spectral bands into a single image based on an assigned color for each pixel of each of the images and a grey level of the images.

2. The method of claim 1, wherein the plurality of spectral bands include emission wavelengths of nicotinamide adenine dinucleotide (NADH) and flavin adenine dinucleotide (FAD).

3. The method of claim 1, further comprising:

identifying the color for each pixel based on the determined value to indicate whether the pixel illustrates cancer.

4. The method of claim 1, further comprising:

determining if other cancers exist based on the identified color for each pixel.

5. The method of claim 1, further compromising:

determining whether the value of each pixel is less than a constant value adjustable for different patient populations.

6. The method of claim 1, further compromising:

configuring a wavelength of the laser beam on the target region to be at three hundred and seventy-five nanometers.

7. The method of claim 1, further compromising:

configuring a transparent sheath over a hand-held probe.

8. The method of claim 1, further comprising:

applying a graphical processing unit to merge the plurality of images into a color-coded image based on a vector representing a spectral shape of spectral bins on a tumor.

9. A system to identify cancer in a target region, the system comprising:

a laser device configured to apply a focused laser beam onto the target region;

a controller that obtains images using each of a plurality of spectral bands of fluorescence induced by the laser beam applied onto the target region;

a processor configured to determine and identify from the plurality of images, a value for each pixel in each of the plurality of images, wherein the value is based on a dimensional vector that represents a spectral shape of a tumor in the target region, and a prevalence of the cancer for each pixel based on the determined value for each pixel in each of the plurality of images; and a merging device configured to merge the images of the plurality of spectral bands into a single image based on an assigned color for each pixel in each of the plurality of images and a grey level of the images.

10. The system of claim 9, wherein the laser device is configured to a single micron spot on the target region for a set time interval.

11. The system of claim 9, further comprising:

a detector configured to receive a reflection of the plurality of spectral bands reflected by a plurality of coated fiber tips.

12. The system of claim 9, wherein the merging device is configured to apply a multi-dimensional vector to merge the images of the spectral bands into the single image.

13. The system of claim 9, wherein the processor is configured to determine the color of each pixel from the plurality of images.

14. The system of claim 9, wherein the processor is configured to determine the prevalence of the cancer for each pixel by comparing the value of each pixel to a numerical constant to identify the color for each pixel.

* * * * *